United States Patent [19]

Gibbons

[11] Patent Number: 4,829,011

[45] Date of Patent: May 9, 1989

[54] AGGLUTINATION ASSAY

[75] Inventor: Ian Gibbons, Menlo Park, Calif.

[73] Assignee: Biotrack, Inc., Mountain View, Calif.

[21] Appl. No.: 90,027

[22] Filed: Aug. 27, 1987

[51] Int. Cl.$^4$ ............... G01N 33/546; G01N 33/555; G01N 33/563

[52] U.S. Cl. ................... 436/512; 436/520; 436/533; 436/534; 436/805

[58] Field of Search ............ 436/512, 533, 534, 520, 436/805

[56] References Cited

U.S. PATENT DOCUMENTS

| | | | |
|---|---|---|---|
| 3,843,776 | 10/1974 | Kamme | 424/12 |
| 4,298,593 | 11/1981 | Ling | 436/512 |
| 4,308,026 | 12/1981 | Mochida | 436/523 X |
| 4,397,960 | 8/1983 | Moussebois | 436/512 |
| 4,556,642 | 12/1985 | Collet-Cassart | 436/512 X |
| 4,596,695 | 6/1986 | Cottingham | 422/58 |
| 4,619,904 | 10/1986 | Giaever et al. | 436/518 |

OTHER PUBLICATIONS

Grubb, et al., Hereditary Serological Human Serum Groups ACTA PATH, et MICROBIOL, SCANDINAV, (1956) vol. unknown, pp. 390–398.

Nisonoff Introduction to Molecular Immunology, Second Edition Sinauer Associates, Inc., Sunderland, Mass., 1984.

Primary Examiner—Sidney Marantz
Attorney, Agent, or Firm—Richard L. Neeley

[57] ABSTRACT

A method of detecting the presence and/or amount (concentration) of an analyte in a sample is provided by forming a reaction medium containing (1) a sample; (2) a plurality of particles having a binding pair member bound to their surfaces; and (3) a monovalent complementary partner to the binding pair member to which is bound an analyte mimic or analyte binding partner; and detecting the presence or amount of agglutination of the particles in the reaction medium. In some cases a polyvalent receptor capable of binding to the analyte (and to the analyte mimic, if present) is also present in the reaction medium.

21 Claims, 3 Drawing Sheets

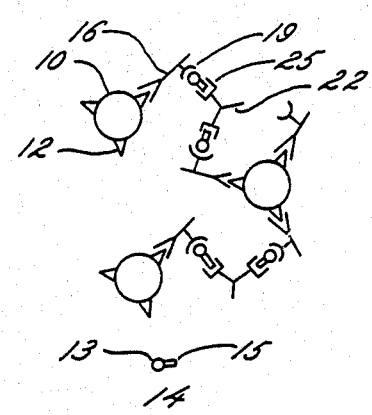
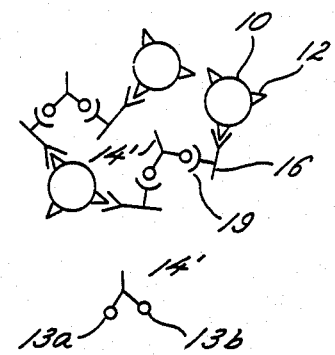
FIG. 2     FIG. 3
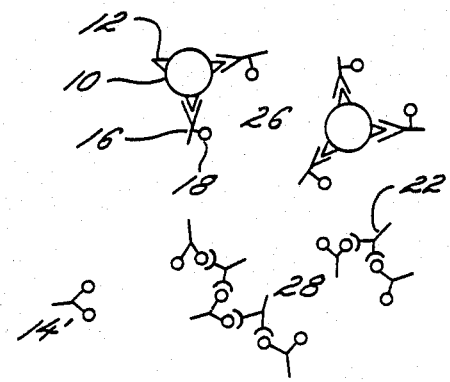
FIG. 4

AGGLUTINATION ASSAY

BACKGROUND OF THE INVENTION

1. Field of the Invention

This invention relates to specific binding assays for analytes in various fluids and particularly to assays that use agglutination as a means of detecting binding.

2. Description of the Background

The use of immunoassays to detect the presence of analytes in various clinical samples has grown explosively in the last few years. Many of these assays have relied upon the use of a radioisotopic label to detect positive reactions between analytes and antibodies. Although the potential hazard for using these reagents is relatively low because of the small amount of radioactivity involved, the equipment required is expensive and complicated and precautions must be taken in disposal of the spent reagents. Reagent instability is also a problem.

The use of enzymes and other non-radioactive labels to produce color reactions has eliminated many of the problems associated with radioactivity. However, color-forming reactions are not appropriate in all media in which assays need to be carried out, such as whole blood. Furthermore, dilution of sample is inevitably required.

Agglutination assays do not require expensive detection equipment, since agglutination can be detected visually. This type of assay was initially developed to determine the presence of specific antigens on red blood cells, for example as with blood typing. In the most commonly used general technique based on agglutination, antibodies are attached to the surface of a solid particle, typically a latex particle, and mixed with a sample. If antibodies on two or more particles can react with an individual polyvalent antigen, a crosslinking will occur between the particles, resulting in the agglutination and/or precipitation of particles. Such agglutination can be detected visually or with instruments. However, such agglutination assays require the labeling of a different latex or other solid particle with a specific immunoglobulin for each type of analyte being detected. Particulate reagents are difficult to make and handle.

Additionally, visually read agglutination assays are non-objective and are usually qualitative. Although it is possible to carry out instrumental (objective) reading of agglutination, the instruments are generally complex and expensive. Furthermore, when whole blood is used as a sample, it is often necessary to remove red blood cells if conventional techniques are used, which increases handling and reduces the convenience of such assays.

Accordingly, there remains room in this field for improved techniques based on agglutination, particularly techniques which do not require the making of different particulate reagents for each analysis or require the removal of red blood cells from whole blood samples and which are readily adaptable to instrumental quantitation.

DESCRIPTION OF RELEVANT LITERATURE

Grubb et al., *Acta. Path. Microbiol. Scand.* (1956) 39:390–398 describes an agglutination assay for hereditary serological human serum groups using an incomplete anti-Rh antibody and red blood cells. Cottingham, U.S. Pat. No. 4,596,695, describes an agglutination reaction chamber through which a fluid undergoing agglutination travels by capillary action. Giaever et al., U.S. Pat. No. 4,619,904, and patents described therein, describe a number of variations of agglutination techniques in which particles of various types are used in agglutination assays. Numerous patents and other publications exist describing the detection and sizing of particles in a fluid stream include Goulas et al., U.S. Pat. Nos. 4,348,111; Adrian, . 4,387,993; Abbott et al., 4,521,521; Lichtenfeld et al., DD No. 232552 A1; Eisenlauer et al., EPA No. 0157310 A2; Brueck, DE No. 3226906 A1; and Bayer AG, UK No. 1516198.

SUMMARY OF THE INVENTION

The present invention provides a method of detecting the presence or amount of an analyte in a sample, which comprises forming a reaction medium containing (1) a sample; (2) a plurality of particles having a binding pair member bound to their surfaces; and (3) a monovalent complementary partner to said binding pair member to which is attached an analyte mimic or analyte binding partner; and detecting the presence of agglutination of said particles in said reaction medium. In some embodiments a polyvalent receptor capable of binding both with the analyte and analyte mimic or with a second binding site on the analyte is also introduced into the reaction medium. The invention is particularly useful for detecting the presence of analytes in whole blood since red blood cells can act as the particles with the normal surface antigen of the red blood cells being used in the assay as the binding pair member. It is also possible to use artificial particles. By changing the analyte mimic or receptor and/or the polyvalent receptor, a number of different agglutination reactions can be carried out without requiring a change in the particles being used for detection or requiring the attachment of different specific substances to the particles.

BRIEF DESCRIPTION OF THE DRAWINGS

The present invention will be better understood by reference to the following detailed description of the invention when considered in connection with the enclosed drawing that forms part of the present specification, wherein:

FIG. 2 is a schematic diagram showing the agglutination complex that results in the presence of analyte during a direct assay. The monovalent complementary partner reacts with one binding site on the analyte, while a polyvalent receptor is present which reacts with a different binding site on the analyte.

FIG. 3 shows the complex that forms in a direct assay using a monovalent complementary partner with a binding site for a polyvalent analyte.

FIG. 4 shows the absence of complex formation in a competition assay when an analyte mimic is present on the monovalent complementary partner and an excess of polyvalent analyte is present.

FIG. 6A is a block diagram of electronic signal processing of a signal received by the detector of FIG. 5, while

DESCRIPTION OF SPECIFIC EMBODIMENTS

The method of the present invention allows use of a single type of particle in multiple assays. Although the method can be used with any particle which has bound to its surface a material that forms a specific binding reaction with a second molecule, the method is particularly useful with whole blood as it can use red blood cells and their cell surface antigens as the particles and binding pair members. In this and many other cases in which a natural particle is present in the sample, the only component of the reaction medium that must be added to the sample is a monovalent complementary partner to the binding pair member that is on the particle surface. In other cases, a polyvalent receptor is also required in order to form an agglutinated complex. Depending on whether one wishes to carry out a direct assay or a competition assay, the monovalent complementary partner is bound to either an analyte binding partner or an analyte mimic, respectively.

The method by which the present invention operates can readily be seen by reference to FIGS. 1-4 and the following detailed description.

FIG. 1 (A and B) illustrates the components of a reaction mixture in which an analyte having a single binding site for the other components of the mixture is present in the sample. The assay shown in FIG. 1 (A and B) is a competitive assay.

Figure 1A:
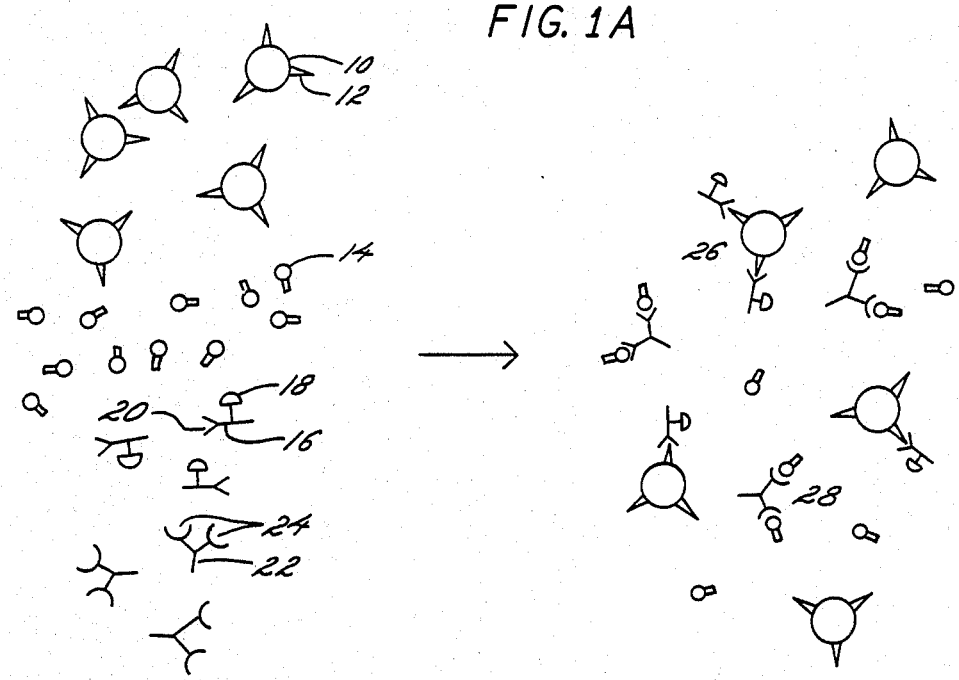
FIG. 1 (A and B) is a schematic diagram showing reactions that occur in the presence (A) and absence (B) of the analyte using an analyte mimic attached to the monovalent complementary partner. The assay is a competition assay in which the antigen presents a single binding site for the added reagents.

FIG. 1A shows formation of a reaction medium containing a plurality of particles 10 having binding pair members 12 bound to their surfaces. In FIG. 1A analyte 14 is present in the sample that is added to the mixture. The reaction mixture includes monovalent complementary partner 16 to binding pair member 12 and analyte mimic 18 attached to complementary partner 16. A single binding site 20 for binding pair member 12 is present on complementary partner 16. Also present is polyvalent receptor 22 with at least two binding sites 24 capable of binding both analyte 14 and analyte mimic 18.

When the components are mixed as shown in the right-hand portions of the figure, a specific binding interaction takes place between the single binding site 20 on monovalent complementary partner 16 and binding pair member 12 on the surface of particle 10. Thus, an initial complex of the type shown as complex 26 in FIG. 1A occurs both in the presence and in the absence of analyte. When analyte is present, as in FIG. 1A, a second complex 28 forms either simultaneously or sequentially according to the assay protocol between the two or more binding sites 24 on polyvalent receptor 22 and the analyte. In the situation shown in FIG. 1A, there is a large excess of analyte so that essentially all of polyvalent receptor 22 is tied up in the form of complex 28 with free analyte 14 remaining in solution. Since the polyvalent receptors are not available to link the particles together, no agglutination occurs.

Figure 1B:
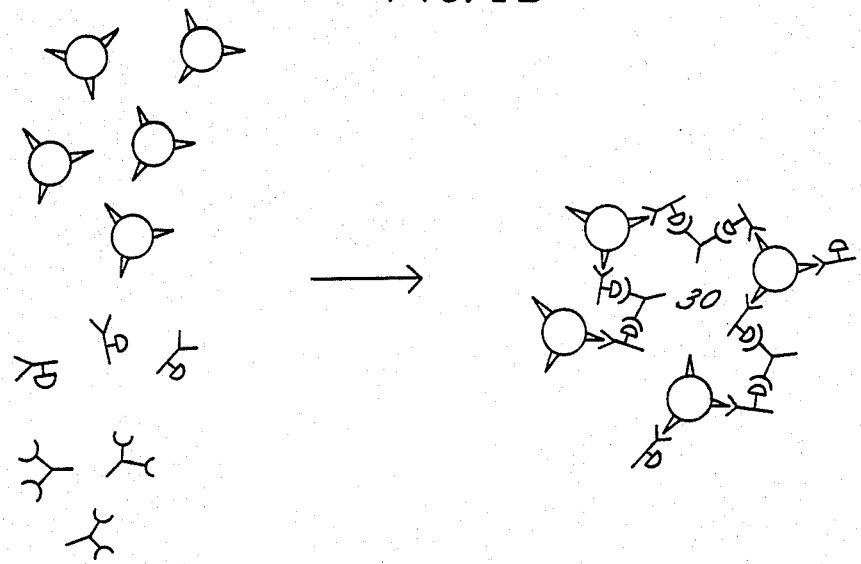

FIG. 1B shows the situation that exists when no analyte is present. The initial complex between the monovalent complementary partner and the binding pair member on the surface of the particle occurs as in FIG. 1A. However, since no analyte is present to bind with the polyvalent receptor, the receptor binds to the analyte mimic. Since the receptor is polyvalent, it is capable of binding with two or more analyte mimics that are in turn bound to different particles through the monovalent complementary binding partner. Accordingly, an agglutinated mass of particles 30 is formed.

Although FIG. 1 shows the two extremes of no agglutination and complete agglutination, it is readily apparent that intermediate amounts of agglutination will occur in the presence of intermediate amounts of analyte.

FIGS. 2-4 show a number of variations of the method of the invention. In all cases, the same particle 10 and binding-pair member 12 are used as well as the same monovalent complementary partner 16 with its specific binding site 20 for binding pair member 12.

In the variation shown in FIG. 2, a direct assay instead of a competition assay is carried out on the same analyte shown in FIG. 1. In order to carry out a direct assay, an analyte binding partner 19 is attached to the monovalent complementary partner 16 rather than the analyte mimic used in the competition assay. Analyte binding partner 19 binds specifically to a first binding site 13 on analyte 14. A polyvalent receptor 22 is provided having two or more binding sites 25 that specifically interact with a second binding site 15 on analyte 14. When analyte is present in a sample, the complex shown in FIG. 2 forms. In the absence of analyte, particles do not agglutinate since analyte 14 and its two binding sites 13 and 15 is required to form a link between particles.

FIG. 3 shows a direct assay using the method of invention to detect the presence of polyvalent analyte. A polyvalent analyte 14' is shown having two identical binding sites 13a and 13b. Particle 10 with binding pair members 12 attached to its surface and monovalent complementary partner 16 with analyte binding partner 19 attached thereto are the same as in FIG. 2. However, no separate polyvalent receptor is required since polyvalent analyte 14' is sufficient to link particles together. The agglutinated complex of particles that occurs in the presence of analyte 14' is shown in FIG. 3.

FIG. 4 shows a competition assay using the same particle 10 with binding pair members 12 attached thereto. The monovalent complementary partner 16 and analyte mimic 18 attached thereto are the same as in FIG. 1. In the presence of an excess polyvalent analyte 14', complex 28 occurs as in FIG. 1 between analyte 14' and polyvalent receptor 22, thereby binding all of the polyvalent receptor. Complex 26 forms between the particles and monovalent complementary partners, but the particles do not agglutinate. In the absence of analyte, a complex similar to 30 of FIG. 1 would form.

The four embodiments set forth above do not represent all possible variations of the invention. Furthermore, it should be noted that the analyte can itself be a molecule normally thought of as a receptor or binding molecule, such as an antibody. For example, the polyvalent receptor in FIG. 1 could represent an antibody having a binding site 24 that interacts with an antigen 18 attached to complementary binding partner 16. This and other variations of the invention can be more readily understood by reference to the following detailed description of the individual components used in carrying out the method of the invention.

The particles used in the method of the invention can be any particle used in agglutination of assays. Particles in a size range of from about 0.1 to 15 $\mu$m are preferred, although larger and smaller particles can be used. Latex particles manufactured specifically for use in agglutination assays are commercially available. Other useful particles include red blood cells (human or animal, fixed or unfixed, naturally present in a sample or added), glass beads, liposomes, pollen spores, metal oxide particles (e.g., titanium oxide), and carbohydrates (e.g., dextrans, agarose, or cellulose). The term latex generally refers to a suspension in water of particles of natural or synthetic rubber or plastic. As far as the practice of the present invention is concerned, the chemical composition of the latex particle is relatively unimportant. Many well-known and commercially available latex particles are prepared by addition polymerization processes in aqueous media. Monomers used in such processes include acrolein, acrylate, methyl acrylate, methacrylate, methyl methacrylate, glycidyl methacrylate, styrene, vinyl toluene, t-butyl styrene, and copolymers containing mixtures of these monomers, the polymers and copolymers optionally containing crosslinking agents such as divinyl benzene and butadiene.

Techniques for preparing such latex particles are well-known as are surface modifications used to attach binding pair members to the particle surfaces. A number of U.S. patents have issued which describe either particles that can be used in the present assay technique, binding partners that can be attached to the particles, and/or coupling methods for attaching the binding partners to the particle surfaces. These include U.S. Pat. Nos. 4,064,088; 4,210,723; 4,264,766; 4,279,617; 3,857,931; 4,062,935; 4,138,213; 4,143,124; 4,162,895; 4,184,849; 4,307,190; 4,253,844; and 4,397,960.

The present invention uses a monovalent reagent that is capable of specifically binding to a substance on the surface of a particle being utilized in the agglutination assay. An analyte mimic or analyte binding partner is attached to the monovalent reagent. The monovalent reagent and the surface-bound binding pair member together form a pair of reagents that exhibit specific binding for each other. Examples of such binding pairs include antigens and antibodies, hormones and receptor proteins, carbohydrates and lectins, antigens and T-cell receptors, complementary nucleic acid strands (DNA-DNA, DNA-RNA, and RNA-RNA), and the like.

It should be noted that the monovalent reagent need not be highly purified. It is possible to use a mixture of specific binding molecules in a mixture containing other binding molecules that are either nonspecific or that bind with different specificities. For example, an antibody fragment obtained from a polyclonal antiserum can be used. The resulting reagent will contain specific antibody fragments capable of binding with the surface-bound binding pair member as well as nonspecific fragments and/or fragments with other specificities. Although sensitivity may be reduced in some circumstances, for example, when non-specific binding uses up some of the polyvalent receptor later described, the assay will still function properly.

Although in many cases it is possible to choose either of the two members of a binding pair as the component present on the particle while using the other to bind to the analyte mimic or analyte binding partner, the selection must be made so as to provide a monovalent material bound to the analyte mimic or analyte binding partner. Using a monovalent material in this part of the assay allows a first binding reaction to occur without itself causing agglutination. This contrasts with many known agglutination assays that use divalent antibodies to react to materials bound to the surface of particles. In such reactions a normal antibody will link two particles together and trigger an agglutination reaction in which cross linking of multiple particles occurs. Divalent antibodies therefore cannot be utilized as the monovalent complementary partner, since uncontrolled agglutination of particles is not desired.

On the other hand, antibody fragments having only one specific binding region are particularly useful for forming the complementary partner to which the analyte mimic or binding partner is attached and represent a preferred embodiment of this aspect of the invention.

A common fragment that can be utilized is the Fab fragment. Fab fragments are well known and are produced by cleaving immunoglobulins with papain. F(ab)' fragments, prepared from immunoglobulins by initially cleaving with pepsin to form divalent F(ab)$_2$' fragments, followed by cleaving with thiol reagents to provide monovalent F(ab)' fragments, are also useful. Genetically engineered univalent fragments are also useful.

When an antibody fragment is used as the monovalent complementary partner in solution, the binding pair member attached to the surface of the particle is the antigen with which the antibody fragment binds. On the other hand, it is also possible to use antibodies bound to the surface of the particle and to use the antigen as the monovalent complementary partner. Since there is no requirement that the substance bound to the surface of the particle be monovalent, either divalent or monovalent antibodies can be used on the particle surface. Monoclonal antibodies are preferred in order to avoid binding of more than one particle to the monovalent complementary partner by having different immunoglobulins from a polyvalent antiserum bind with different portions of the same antigen. For example, a complex protein utilized as an antigen would have more than one determinant that could react with different antibodies in a polyclonal antiserum on the surface of particles. However, if a monoclonal antibody that reacts with only one determinant is used, a complex complementary partner with multiple determinants can be used without danger of interfering with correct interpretation of agglutination reactions; i.e., the complex component would still be monovalent with respect to its ability to react with the binding pair member (antibody) on the surface of the particle.

Techniques for attaching biological molecules, such as binding pair members as discussed above, to solid surfaces or other soluble biological molecules are well known and need not be discussed here in detail. Examples include using non-covalent interactions (e.g., hydrophobic interactions with a hydrophobic surface); covalent attachment (e.g., using a reactive group that reacts with an amino, carboxylic acid, hydroxy, or other functional group present in an amino acid side chain, carbohydrate moiety, or other portion of the binding pair member); and various linking compounds (usually bi-functional) that are capable of reacting both with the binding pair member and the surface of the solid particle or soluble monovalent reagent. For example, numerous examples of techniques that can be used to form attachments between binding pair members and solid surfaces are set forth in "Uniform Latex Particles" (1984), Leigh B. Bangs, Seragen Diagnostics, Inc., Indianapolis, IN 46206.

The monovalent complementary partner is attached to another moiety in the reaction medium, namely either a material that mimics the analyte or that specifically binds to the analyte. In many cases the analyte mimic will be an actual molecule of the analyte attached covalently to the monovalent complementary partner. For example, a digoxin molecule can be attached through its sugar residues after activation with periodates to a free amine group of an Fab immunoglobulin fragment and used in a digoxin assay. Intermediate divalent linking agents can be used, for example having an N-hydroxysuccinimide ester group at one end to react with an amino group on the analyte mimic and a maleimide group at the other end to react with a free sulfhydryl group of an Fab' immunoglobulin fragment. Specific techniques for attaching typical analytes found in whole blood to immunoglobulins, a preferred aspect of the present invention, are set forth in Conn, N., in *Methods in Enzymology* (1983) 103:49–58.

It is also possible to use a molecule other than the analyte as an analyte mimic. For example, short oligopeptides can be used to replace viral particles or bacterial surface antigens. An example of this is set forth in U.S. Pat. No. 4,629,783, which describes synthetic antigens for the detection of AIDS-Related Disease. The relatively short oligopeptides described in this patent can be readily prepared synthetically or by genetic engineering techniques, and it is not necessary to use a whole HTLV-III viral particle. In a similar manner, other analyte mimics that are capable of being recognized by the polyvalent receptor (described later) in a specific binding interaction can be used in place of the actual analyte since it is the recognition of the analyte and the analyte mimic by the polyvalent receptor that is important, not the actual structure of the analyte.

Analyte mimics attached to a solid surface or to a soluble material are well known and do not represent new technology by themselves although their use in an assay of the present type was not previously known.

When an analyte binding partner is used instead of an analyte mimic, the analyte binding partner can be any molecule capable of binding specifically with the analyte. Accordingly, this binding partner will vary extensively with the type of analyte. The analyte and analyte binding partner can be, for example, any of the types of binding pairs described previously. The analyte binding partner can be attached to the soluble monvalent complementary partner as described above for other biological molecules that are joined together.

One useful means for preparing a univalent complementary partner attached to an analyte binding partner is to prepare a divalent antibody having two specificities. Such antibodies can be prepared from normal antibodies by cleaving the disulfide links between chains and reforming disulfide links between antibody chains having different specificities. Such antibodies can also be produced by preparing quadroma or trioma cell fusion products, which secrete such antibodies. Recombinant monoclonal antibodies of this type and methods for producing them are described in U.S. Pat. No. 4,474,893. Also see Brennan et al., *Science* (1985) 229:81–83.

Some embodiments of the invention use a polyvalent receptor capable of specifically binding either with the analyte and with the analyte mimic. This polyvalent receptor can be an antibody to the analyte (and thus be polyvalent) but can also represent other types of proteins and other substances capable of reacting with an analyte that would be present in a sample. If only monovalent receptors are available (for example, a monovalent cell surface receptor capable of binding with a hormone), it is possible to use either direct bonding or linking agents (such as a soluble polymer containing reactive groups) to attach two or more monovalent receptors together to form a polyvalent receptor.

A polyvalent receptor is not required in all embodiments of the invention. For example, the embodiment shown in FIG. 3 shows a divalent analyte that serves as a linking group between particles. Accordingly, a polyvalent receptor is not required when a polyvalent analyte is present in a direct assay in which an analyte binding partner is used. However, divalent receptors capable of binding with the analyte (and analyte mimic, when present) are required in other embodiments, such as those shown in FIGS. 1, 2, and 4.

The polyvalent receptor will serve different functions depending on the type of assay in which it is used. In a competition assay such as that shown in FIG. 1, the polyvalent receptor will function to react with the analyte mimic if the analyte is not present in the sample being tested. Since the receptor is polyvalent, it will bind to two or more analytes or analyte mimics. Since the analyte mimics are attached to the particles by means of the monovalent complementary partner and its binding pair member, the polyvalent receptor is capable of binding particles together and causing agglutination to occur. Agglutination can then be detected by standard means or by the special techniques described later in detail. The degree of agglutination will be reduced as the amount of analyte present in the sample increases, in a manner analogous to that which occurs for other types of competitive binding assays.

In the embodiments shown in FIG. 2, the divalent receptor forms an agglutination complex by reacting with a binding site on the analyte different from the binding site by which the univalent complementary partner attaches to the analyte (through its covalently attached analyte binding partner). In the embodiment shown in FIG. 4, the polyvalent receptor functions in the same manner as in the embodiment shown in FIG. 1.

It should be recognized that the four embodiments shown in FIGS. 1–4 do not represent all embodiments of the invention. For example, it is possible to use a mixture of monovalent complementary partners having two or more different analyte binding partners attached thereto. Each type of analyte binding partner would react with a different determinant on the analyte. In such a case, the analyte is polyvalent and can aid in the formation of an agglutination complex similar to that shown in FIG. 3 but with each of the binding sites 13a and 13b of the polyvalent antigen 14' representing a different type of determinant. If a mixture of monovalent complementary partners having analyte binding partners specific for each of the determinants is present, an agglutinated complex of particles will form in the presence of analyte.

The reaction medium to which other components are added may be the naturally-occurring medium of the sample or the sample may be introduced into a liquid medium, for example to provide for the desired characteristics necessary for the capillary pumping action and the detectable signal described later for preferred embodiments. For the most part, aqueous media will be employed, and to that extent aqueous media will be exemplary of the media employed in the subject invention. The aqueous media may be modified by the addition of a variety of miscible liquids, particularly oxygenated organic solvents, such as lower alkanols, dimethyl formamide, dimethyl sulfoxide, acetone, or the like. Usually, the organic solvents will be present in less than about 40 volume percent, more usually in less than about 20 volume percent. Besides other solvents, other liquid or solid additives may be included in the medium to modify the flow or other properties of the medium, such as sugars, polyols, polymers, detergents, surfactants and the like, involved with changes in wetting, adherence, laminar flow, viscosity, and the like.

In addition to the components mentioned above, other additives may be included for specific purposes. Buffers may be desirable to maintain a particular pH. Enzyme inhibitors may be included. Other reagents of interest are preservatives, stabilizers, activators, enzyme substrates and cofactors, oxidants, reductants, and antioxidants.

A preferred embodiment would use dried reagents to which a sample or diluted sample would be added. Agglutination could be determined after adding sample directly to a reaction vessel containing dried reagents, thereby simplifying the assay protocol.

The present invention allows the use of a single type of particle having a binding pair member either artificially bound to its surface or naturally forming a part of its surface in a number of different assays without regard to the type of analyte being detected. To detect different analytes, monovalent complementary partners attached to analyte mimics or binding partners are used, a different analyte mimic or analyte binding partner being used for each analyte. However, it is possible to use a single type of monovalent complementary partner and merely to change the analyte mimic or analyte binding partner that is attached to this complementary binding partner. A different polyvalent receptor capable of binding with the analyte and the analyte mimic is also required for each type of analyte, if an assay type requiring a polyvalent receptor is selected. However, these soluble components can be provided and used with the same particles.

The method of the present invention can be used with any type of sample that is capable of being used in an assay that relies on a specific binding reaction between members of a binding pair. The method is particularly useful for biological samples but is not limited to such use. Industrial waste waters, natural waters, samples of air-borne particles, and industrial chemical reaction media can all be tested utilizing the present method. However, preferred samples include samples of biological origin, particularly samples of blood, urine, feces, sweat, tissue, sputum, wound drainage, and the like for analysis in clinical assays.

The analyte itself can be any material that is capable of undergoing a binding reaction with a binding partner. There is otherwise no limit on the analyte. Since immunoglobulins can be created which react specifically with numerous analytes, the types of analytes that can be determined using the method of the present invention is practically unlimited. Examples of analytes include glucose (utilizing a lectin as a receptor), cortisol (utilizing a cell surface cortisol receptor), human chorionic gonadotropin (hCG, utilizing a monoclonal antibody as a receptor), and lidocaine (utilizing a polyvalent antiserum as a receptor). Other analytes include small organic molecules, such as drugs, hormones, steroids, neurotransmitters, growth factors, commercial chemicals, degradation products, drugs of abuse, metabolites, catabolites, etc. Large organic molecules may be determined, such as nucleic acids, proteins, polysaccharides, or the like. Aggregations of molecules may also be of interest, particularly naturally-occurring aggregations such as viroids, viruses, cells, both prokaryotic and eukaryotic, including unicellular microorganism, mammalian cells such as lymphocytes, epithelial cells, neoplastic cells, and the like.

The invention can be used in a qualitative sense merely to detect the presence of an analyte in a sample or in a quantitative sense. When used in a qualitative sense, the reaction medium containing the various components is merely checked for the presence or absence of agglutination. Agglutination in a competitive assay or lack of agglutination in a direct assay indicates that the analyte is not present at a preset concentration while the opposite indication shows the presence of analyte at that concentration or higher. The concentration of analyte that will just cause agglutination is first selected, after which the concentration of other components can be adjusted to provide the agglutination/no agglutination signal.

The method can also be practiced quantitatively by measuring the amount of agglutination that takes place or the rate of agglutination. The measurement of the amount of analyte present can either be semiquantitative or quantitative. Semiquantitative measurements are typically carried out by using a series of dilutions of the sample and determining at what dilution or dilutions agglutination occurs. This is typically referred to as the titer of the sample. Dilutions are usually serial with the result that each titer is a doubling or some other multiple of the previous one. A series of dilutions might, for example, be 1:1, 1:2, 1:4, 1:8, 1:16, 1:32, 1:64, and 1:128. A 1:64 titer would therefore represent a situation in which no agglutination was seen in the 1:128 dilution but agglutination was seen in the 1:64 dilution.

Quantitative analysis is generally carried out by using instruments capable of reading light scattering. Such instruments have been on the market for some time and are manufactured by a number of sources. It is also possible to carry out a quantitative agglutination reaction of the invention in a device specifically designed for unskilled use that is set forth in U.S. patent application Ser. Nos. 762,748, filed Aug. 5, 1985, and 880,793, filed July 1, 1986.

These patent applications describe fabrication techniques, the resulting devices, and techniques related to the use of devices in which a defined chamber or channel is prepared within the internal space of a solid device. The devices typically call for the use of capillary force to draw a sample into the internal chambers of a plastic device. Such capillary flow devices, particularly capillary flow devices designed for a constant flow rate, typically include at least one capillary acting as a pump, usually for controlling the volume of the sample and the time period for reaction; a chamber; an inlet port; a vent; and a reagent in proximity to at least one surface of the device. The capillary and chamber provide for capillary flow due to surface action and for mixing of the assay medium with the reagent. The reagent is part of a detection system, whereby a detectable result occurs in relation to the presence of an analyte. In the present case the reagent would provide any components of the reaction medium not provided by the sample itself.

The sample will be introduced into the device through an inlet port, which may introduce the sample into a chamber or a capillary. The sample will then transit the device passing through the capillary(ies) or chamber(s), where the sample will encounter the reagents necessary for forming the agglutination reaction medium. By having orifices which connect the pathway to the atmosphere at one or more sites, one can terminate or otherwise control the flow up to or past that site.

The measurement of scattered light can be used to measure a change in the size population of particles in a sample passing through the capillary device. This can be particularly useful for measurement of agglutination. When a laser beam is passed through the sample, a detector is able to distinguish particle size without a change in the flow rate. Small particles produce signals with high frequency and a low amplitude; large particles (agglutinated particles) give signals of lower frequency (fewer total particles) and a higher amplitude (each particle is larger). Thus the change in particle size distribution may be detected by integrated noise employing known circuitry.

Numerous other detection techniques could be used with agglutination where the particle is a red blood cell or other particle to which particular antigens are or have been bound. For example, as the accretion of particles increases, ultimately a plug will form in a capillary channel or filter and flow will stop. The rate of formation of the plug will vary depending upon the concentration of analyte. Other techniques are discussed in the relevant publications listed in the Relevant Literature section of this specification.

Figure 5:
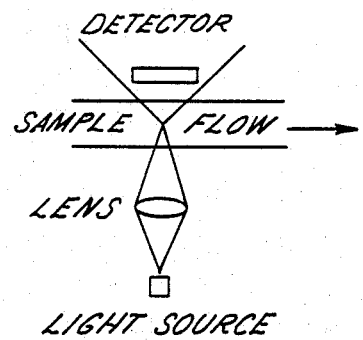
FIG. 5 is a schematic diagram illustrating light source and detector configuration when agglutination is measured in a capillary flow device.

The construction and use of an exemplary detector for a capillary flow agglutination device can be seen by referring to FIG. 5, which shows a cross sectional view of a sample flow channel through which a reaction mixture is flowing. The particles utilized in the present invention (whether they are artificial or come from a sample) have a different refractive index and/or significantly higher absorption coefficient as compared with the fluid being analyzed. When this reaction medium flows across the focus of a light beam with a beam waist comparable to the particle size, the light will be attenuated due to scattering and/or absorption. When particles are not clustered (the case of no agglutination), tbe light impinging on a photodetector located above the reaction medium and in the path of the columated light will be constant.

When the particles agglutinate, the average effective size of particles present in the reaction medium will no longer be constant. On the microscopic scale, the light attentuation fluctuates. Detection of these fluctuations allows a quantitative measurement of the level of agglutination in the sample.

For example, a germanium arsenic semiconductor laser can be utilized as a light source. By using a laser, low power consumption and small spot sizes are achieved. Germanium arsenide semiconductor lasers can form spot sizes of only a few microns, very similar to the size of a red blood cell. By sizing the spot to coincide with the size of the particles present prior to agglutination, high sensitivity is achieved.

Figure 6A:
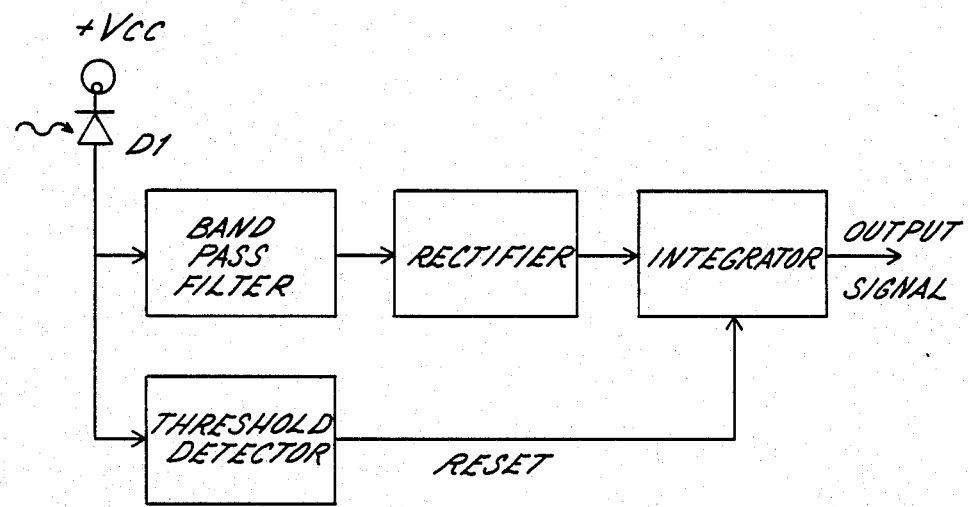

In order to prevent minor fluctuations resulting from individual particles interfering with the passage of light through the reaction medium from indicating a signal, the original signal from the detector is fed to a band pass filter as shown in FIG. 6A. The band pass filter can resolve the agglutination signal from background noise and the small fluctuations caused by scatter from individual particles.

The fluctuations resulting from agglutination are rectified (converted from an alternating signal to a unipolar signal) and integrated over time. A measurement interval (typically about 20 sec) is selected with a longer integration time (typically about 60 sec.) in order to provide a smooth output signal. The output of the integrator is the time average of the fluctuations due to agglutination.

Figure 6B:
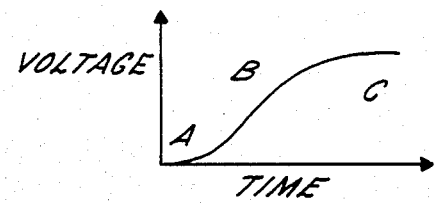
FIG. 6B shows the output signal from the signal processor of FIG. 6A.

A graph of the output voltage versus time is set forth in FIG. 6B. Initial output is quite low corresponding to the flow of unagglutinated particles. As particles begin to cluster, photodetector fluctuation will increase as shown in region B of the graph. The slope of this region indicates the rate of the agglutination reaction. Region C shows the voltage present for the final level of agglutination after the reaction has reached its end point.

In summary, this method of detecting agglutination comprises passing a focused beam of light through a predetermined pathlength of a fluid containing particles whose agglutination is being detected, the beam being of similar cross-sectional area to the cross-sectional area of one of the particles, while the particles and beam are in relative motion (usually as a result of fluid flow in a capillary or other small channel); detecting fluctuations in light transmitted through the fluid; and resolving a signal produced by the presence of agglutinated particles, which produce large fluctuations in transmitted light, from background fluctuations in transmitted light produced by individual particles.

The flow in the capillary channel unit can also be detected by various techniques which allow for detection of fluid flow, e.g., optical sensors, flow sensors or pressure sensors, or by having a detectable component in the assay medium, which can be detected visually or by diode assay. Techniques which allow for fluid flow determinations include the use of means for measuring triboelectricity, means for detecting the rate of passage of liquid, detecting Doppler effects, or the like. Preferably, a component is used in the medium which allows for flow detection by detecting the passage of the component through the first capillary channel exiting a receiving chamber.

Various kits for detecting analytes can be prepared using associated reagent combinations. Such kits will generally comprise a multi-reagent container, which can be a multi-chamber container, a holder designed to retain multiple individual containers, or the like, by which various combinations of reagents of the invention can be associated with each other and used in an analysis. Typical individual reagents can be selected from (1) monovalent complementary partners having either an analyte mimic or analyte binding partner bound thereto; (2) polyvalent receptors; (3) particles having binding pair members bound to their surfaces; (4) control samples (negative controls without analyte or positive controls containing specified amounts of analyte); and (5) diluents (e.g., stock or diluted buffers for use in preparing reaction media), among others. Kits can be designed for detection of a single analyte, or multiple components can be provided in order to allow a single kit to detect multiple analytes. Other components of the kit can include empty containers for measuring, mixing, or reacting various components; capillary flow devices for carrying out analyses according to the preferred embodiments of the invention; printed instructions directing the user to carry out the method of the invention; or monitoring devices (e.g., optical/electronic devices) for detecting agglutination. Such kits can provide a complete system for detecting an analyte or can represent a portion of a complete system (e.g., containing only depletable reagents and/or disposable parts of the total system).

The invention now being generally described, the same will be better understood by reference to the following examples which are provided for purposes of illustration only and are not intended to be limiting of the invention.

EXAMPLE 1

Purification of Anti-Lidocaine

Goat anti-serum to lidocaine-human serum albumin (HSA) was obtained from Kallestad Laboratories, Inc. The IgG fraction was purified using a DEAE-Sephacel® column. One ml of anti-lidocaine serum was mixed with 60 μl of 5 mM bromophenol blue as a control of the fractionation procedure. The serum was dialyzed against the starting buffer (0.0175M phosphate, pH 6.8) for one-hour and then applied to a 10 ml DEAE-Sephacel column previously equilibrated with the starting buffer. The IgG fractions eluted with the starting buffer were pooled and concentrated by dialysis against a solution of saturated ammonium sulfate. The precipitate was collected by centrifugation and resuspended in a minimal volume of water. The resulting solution was dialyzed against saline. Further concentration of the IgG was performed using Amicon Centricon-30 microconcentrators. The final concentration of IgG was 50 mg/ml, as determined by O.D. 280.

Preparation of the Fab Fragment of Rabbit Anti-(Human Red Blood Cell)

Fab fragments were prepared from the IgG fraction of rabbit anti-human-red-blood-cell antiserum (Cappel) using a variation of the method described by Porter, *Biochem. J.* (1959) 73:119. IgG (10 mg/ml) was enzymatically cleaved to Fab and peptide fragments by incubation at 37° C. in a solution containing 10 mM phosphate, pH 7.3, 0.15M sodium chloride, 1 mM EDTA, 25 mM β-mercaptoethanol and 3 mg/ml papain (Sigma). After one hour the digestion was stopped by the addition of iodoacetamide to a final concentration of 30 mM.

The Fab fragments were purified as described by Mage, Methods in Enzymology (1970) 70:142. The protein digest was first dialyzed against 50 mM acetate, pH 5.5, and then applied to a CM-sephadex column (12"×1"). The Fab fraction was eluted with 50 mM acetate, pH 5.5, and the Fab-containing fractions were pooled and concentrated by dialysis against saturated ammonium sulfate. The Fab was further purified using Bio-Rad Affi-gel® protein-A affinity column as described in the manufacturers' directions. The purified Fab was concentrated and resuspended in saline containing 0.01% sodium azide.

Preparation of the Fab-Lidocaine Conjugate

Under nitrogen, 25 mg (65 μmoles) of p-aminolidocaine hemisuccinamide (Molecular Probes) was dissolved in 500 μl dry N,N-dimethylformamide. The mixture was cooled to −10° C. and 18 μl of triethylamine was added. After the resulting mixture was stirred for 30 minutes, 9 μl of dry isobutyl chloroformate was added and the stirring was continued at −10° C. After 90 minutes 294 μl of the resulting mixed anhydride was added to 3 ml of an ice-cold solution of Fab (7 mg), pH 8.5. The solution was left to mix in the cold for 2 hours with dilute sodium hydroxide being added on demand to maintain the pH at 8.5. The mixture was then dialyzed against 0.1M sodium carbonate, pH 8.5, followed by dialysis against water and finally against saline.

A hapten number of 23 was found by measuring the number of primary amino groups blocked as determined by the TNBS assay as described in Habeeb, *Analyt. Biochem.* (1966) 14:325.

EXAMPLE 2

Lidocaine Assay

The dose response of the assay of the invention to free lidocaine in blood was determined as follows. Whole human blood, anticoagulated with sodium EDTA, was spiked with free lidocaine such that the final concentration of lidocaine in the blood ranged from 0 μg/ml to 20 μg/ml. To a 50 μl sample of the blood, 5 μl of FAB-Lidocaine conjugate (1.8 mg/ml) was added and incubated for 1'. Then, 5μl of anti-lidocaine (8.6 mg/ml protein) was added, mixed and allowed to incubate for a minute. The sample was then applied to the application well of a blank Protime capillary flow cartridge, which was used to detect agglutination. The Protime cartridge used was the same as a commercial Protime cartridge used for measuring prothrombin time but did not contain any reagent. The cartridge merely provided a flow path. The Protime cartridge, which is commercially available from Biotrack, Inc. of Sunnyvale, California, is described in U.S. patent application Ser. Nos. 762,748 and 880,793, described above. Agglutination was monitored by passing light from a germanium arsenide semiconductor laser, focused with a lens to provide a beam waist approximately the size of a red blood cell, through the first capillary of the capillary flow cartridge. Light was measured by a detector and analyzed as describe in FIGS. 5 and 6 and the accompanying text. The integrated signal produced a straight line the slope of which was directly proportional to the degree of agglutination. This is termed the slope of agglutination, and these values vs. the concentration of free lidocaine in the blood are presented in Table 1. An increase in agglutination with decreasing lidocaine concentration is seen as would be expected. Unknown values can be determined by graphing the data set forth in Table 1 and reading the unknown concentration from the graph using the slope of agglutination for the sample containing the unknown lidocaine concentration.

TABLE 1

| Added Lidocaine μg/ml | Slope of Agglutination | N(1) |
|---|---|---|
| 20 | 0.07 ± 0.02 | 5 |
| 10 | 0.12 ± 0.02 | 5 |
| 5 | 0.22 ± 0.04 | 5 |
| 2.5 | 0.24 ± 0.05 | 5 |
| 1.2 | 0.46 ± 0.12 | 4 |
| 0.62 | 0.48 ± 0.20 | 5 |
| 0.31 | 0.52 ± 0.05 | 4 |
| 0.15 | 0.63 ± 0.06 | 5 |

(1)N = number of replicates.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of detecting the presence or amount of an analyte in a sample, which comprises:

forming a reaction medium containing (1) a sample; (2) a plurality of particles having a binding pair member bound to their surfaces; and (3) an analyte mimic or analyte binding partner bound to a monovalent complementary partner to said binding pair member;

detecting agglutination of said particles in said reaction medium; and correlating agglutination with presence of said analyte In said sample if said method is a direct assay and with absence of said analyte if said method is a competitive assay.

2. The method of claim 1, wherein an analyte mimic is bound to said monovalent complementary partner and said reaction medium further comprises a polyvalent receptor capable of binding both with said analyte and with said analyte mimic.

3. The method of claim 2, wherein said analyte comprises a single binding site reactive with said polyvalent receptor.

4. The method of claim 1, wherein an analyte binding partner is bound to said monovalent complementary partner.

5. The method of claim 4, wherein said analyte comprises a plurality of binding sites reactive with said analyte binding partner.

6. The method of claim 4, wherein said analyte comprises a single binding site reactive with said analyte binding partner and said reaction medium further comprises a polyvalent receptor capable of binding to a second site on said analyte different from the site reactive with said analyte binding partner.

7. The method of claim 1, wherein said sample naturally contains said particles.

8. The method of claim 4, wherein said sample is whole blood.

9. The method of claim 1, wherein said complementary partner is a monovalent immunoglobulin fragment.

10. The method of claim 9, wherein said fragment is specific for a red blood cell surface antigen.

11. The method of claim 1, wherein said particle is a latex particle.

12. The method of claim 2, wherein more than one analyte mimic is bound to said complementary partner.

13. The method of claim 1, wherein said polyvalent receptor is a polyvalent immunoglobulin.

14. The method of claim 1, wherein said binding pair member is a polyvalent immunoglobulin.

15. The method of claim 1, wherein said monovalent complementary partner comprises a mixture of monovalent complementary partners of different types, each type having the same monovalent binding specifity but comprising an analyte binding partner specific for a different determinant of the same antigen.

16. The method of claim 1, wherein detecting agglutination is by visual inspection.

17. The method of claim 1, wherein detecting agglutination is by electronically measuring light transmitted, reflected, or scattered by said reaction medium.

18. A regeant combination for use in the detection of an analyte, comprising (1) a monovalent complementary partner to a member of a complementary binding pair, said complementary partner having bound thereto an analyte mimic or analyte binding partner, and (2) either (a) a polyvalent receptor capable of binding with said analyte and with said analyte mimic or (b) a plurality of particles having said binding pair member bound to their surfaces.

19. The reagent combination of claim 18, wherein said complementary partner is a monovalent immunoglobulin.

20. The reagent combination of claim 18, wherein said analyte mimic bound to said complementary partner is a molecule of said analyte covalently attached to a monovlaent immunoglobulin.

21. The reagent combination of claim 18, wherein each member of said reagent pair is present as a dry reagent in an analytical device designed for the measurement of agglutination.

* * * * *

UNITED STATES PATENT AND TRADEMARK OFFICE
CERTIFICATE OF CORRECTION

PATENT NO.  : 4,829,011
DATED       : May 9, 1989
INVENTOR(S) : Gibbons

It is certified that error appears in the above-identified patent and that said Letters Patent is hereby corrected as shown below:

In column 11, line 38, "tbe" should read --the--.

In column 15, line 18, "In" should read --in--.

In column 16, line 24, "regeant" should read --reagent--.

Signed and Sealed this

Twentieth Day of February, 1990

Attest:

JEFFREY M. SAMUELS

*Attesting Officer*         Acting Commissioner of Patents and Trademarks